US012797501B2

(12) United States Patent
Tchakalova et al.

(10) Patent No.: US 12,797,501 B2
(45) Date of Patent: Nov. 17, 2026

(54) SANITIZER DISPENSER

(71) Applicant: Firmenich SA, Satigny (CH)

(72) Inventors: Vera Tchakalova, Satigny (CH); Aude Daugeron-Jouault, Neuilly-sur-Seine (FR); Laura Mesmin, Satigny (CH); Margot Stafford, Neuilly-sur-Seine (FR); Addi Fadel, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 335 days.

(21) Appl. No.: 18/568,408

(22) PCT Filed: Jun. 7, 2022

(86) PCT No.: PCT/EP2022/065389
§ 371 (c)(1),
(2) Date: Dec. 8, 2023

(87) PCT Pub. No.: WO2022/268491
PCT Pub. Date: Dec. 29, 2022

(65) Prior Publication Data

US 2024/0277879 A1 Aug. 22, 2024

Related U.S. Application Data

(60) Provisional application No. 63/212,901, filed on Jun. 21, 2021.

(30) Foreign Application Priority Data

Jun. 30, 2021 (EP) .................................... 21182637

(51) Int. Cl.
*A61L 2/18* (2026.01)
*A61K 8/04* (2006.01)
*A61L 103/05* (2026.01)

(52) U.S. Cl.
CPC ................ *A61L 2/18* (2013.01); *A61K 8/042* (2013.01); *A61K 2800/884* (2013.01); *A61L 2103/05* (2026.01); *A61L 2202/15* (2013.01)

(58) Field of Classification Search
CPC ................................. A61L 2/18; A61K 8/042
See application file for complete search history.

(56) References Cited

U.S. PATENT DOCUMENTS

2002/0193321 A1 12/2002 Vishnupad et al.
2011/0036867 A1 2/2011 Flores
(Continued)

FOREIGN PATENT DOCUMENTS

WO WO-2019077052 A1 * 4/2019 ............ A61K 8/342

OTHER PUBLICATIONS

International Search Report and Written Opinion for corresponding International Application No. PCT/EP2022/065389 dated Sep. 29, 2022 (14 pages).

*Primary Examiner* — Sean E Conley

(57) ABSTRACT

The invention relates to a sanitizer dispenser (1, 1') and to a method for sanitizing with such a sanitizer dispenser (1, 1'). The sanitizer dispenser (1, 1') comprises: a container body (10) with a first compartment (11) and a second compartment (12), which are separated from one another, wherein the first compartment (11) contains a sanitizer substance (20), and wherein the second compartment (12) contains a hydrating substance (30); and a dispenser outlet (50, 50') attached to the container body (10) and configured to dispense the sanitizer substance (20) from the first compartment (11) and the hydrating substance (30) from the second compartment (12).

18 Claims, 4 Drawing Sheets

(56) References Cited

U.S. PATENT DOCUMENTS

Figure 1:
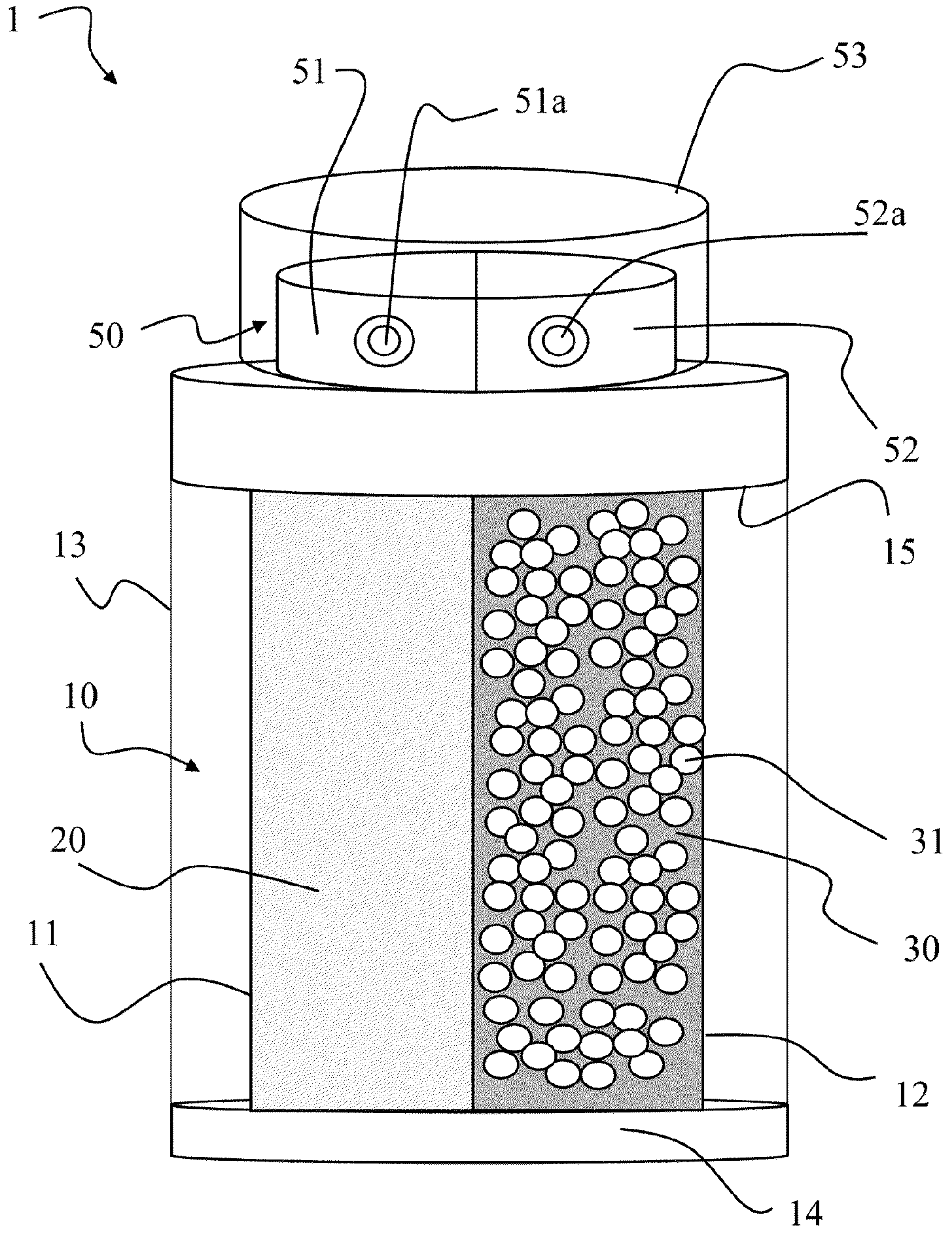

| | | | |
|---|---|---|---|
| 2020/0238244 | A1 | 7/2020 | Tchakalova et al. |
| 2021/0094054 | A1 | 4/2021 | Noar |

* cited by examiner

SANITIZER DISPENSER

CROSS REFERENCE TO RELATED APPLICATIONS

The present application is a U.S. national phase entry under 35 U.S.C. § 371 of PCT Application No. PCT/EP2022/065389, filed Jun. 7, 2022, which claims the benefit of priority of U.S. Provisional Application No. 63/212,901, filed Jun. 21, 2021, and of European Application No. 21182637.5, filed Jun. 30, 2021. The entire contents of these applications are explicitly incorporated herein by this reference.

FIELD OF THE INVENTION

The present invention relates to a sanitizer dispenser and a method for sanitizing with such a sanitizer dispenser.

TECHNICAL BACKGROUND

Sanitizing is required for killing or inactivating pathogens such as viruses, bacteria, and microorganisms. Especially epidemic or pandemic situations such as the Coronavirus Disease 2019 (COVID-19) pandemic require the frequent skin application of a sanitizer substance. Such a sanitizer substance may be virucide and may be provided in the form of a solution. However, such substances are harmful for the skin, provoking strong skin dehydration and the consecutive dermatological diseases. In addition, they have an unpleasant odor.

Therefore, it is an object of the present invention to overcome the afore-mentioned drawbacks. That is, it is in particular an object of the present invention to provide a solution for sanitizing, which prevents dehydration and an unpleasant odor.

These and other objects, which become apparent upon reading the following description, are solved by the subject matter of the independent claims. The dependent claims refer to preferred embodiments of the invention.

SUMMARY OF THE INVENTION

According to the invention, a sanitizer dispenser is provided. The sanitizer dispenser comprises: a container body with a first compartment and a second compartment, which are separated from one another, wherein the first compartment contains a sanitizer substance, and wherein the second compartment contains a hydrating substance; and a dispenser outlet attached to the container body and configured to dispense the sanitizer substance from the first compartment and the hydrating substance from the second compartment.

Hence, the sanitizer dispenser includes in a single device both the configuration to dispense the sanitizer substance (i.e., a hygiene function), and the configuration to dispense the hydrating substance (i.e., a skin hydration function). The latter function at the same time may effect a pleasant odor. The dispenser may be used for application of the substances on a surface (e.g., a skin). The dispenser can be used by a user to consecutively or at least in part at the same time, i.e. simultaneously, dispense the respective substances on a surface, such as a skin. Therefore, the dispenser facilitates an easy sanitization and at the same time includes a solution for preventing the skin from dehydration and from becoming an unpleasant odor. Since the compartments are provided by the container body, the provided solution is furthermore advantageous with respect to compactness and handiness. For example, the container body may include one or more walls, which divide the container body into the different compartments, i.e., the one or more walls may be arranged such that they delimit the compartments. Further, the sanitizer dispenser improves the aesthetics of the final product, i.e. of the combination of a sanitizer substance with a hydrating substance.

The dispenser outlet may be configured such that, upon operation of the dispenser outlet, both the sanitizer substance dispenses from the first compartment and the hydrating substance dispenses from the second compartment. Thereby, the dispenser may (e.g., automatically) dispense both substances by a single operation of a user. Hence, the dispenser can be very conveniently used. For example, the configuration of the dispenser outlet is such that, upon operation of the dispenser outlet, dispensing the sanitizer substance happens at least in part before and/or at least in part simultaneously to dispensing the hydrating substance. Hence, the dispenser outlet dispenses the substances in a defined sequence, thereby providing a sufficient sanitization and hydration of the skin, in particular without the user requiring an operation of the dispenser in a specific manner. Simultaneous dispensing of the substances may be such that the substances are mixed with one another, e.g. as they flow through and/or are discharged from the dispenser outlet. For example, the dispenser outlet may comprise a dispensing outlet for discharging the substances from the sanitizer dispenser, wherein the substances may mix (or combine or merge) upstream the dispensing outlet, in the dispensing outlet, and/or downstream the dispensing outlet. Thus, the substances (e.g., fluidic or liquid) may combine in the dispensing outlet just prior to administration to the skin or be administered sequentially to combine on the skin.

The dispenser outlet may comprises a first section and a second section, which are independently operable from one another, wherein the first section is operable to dispense the sanitizer substance, and wherein the second section is operable to dispense the hydrating substance. Hence, the dispenser outlet can be easily used for selectively dispensing the sanitizer substance or the hydrating substance. For instance, the first section and second section can be used for consecutive dispensing and thus application of the sanitizer substance and hydrating substance.

The first section is arranged preferably adjacent to the second section. Thereby, the dispenser outlet and thus the sanitizer dispenser can be downsized.

The dispenser outlet may comprise a section operable to dispense both the sanitizer substance and the hydrating substance, preferably via a single dispensing opening. For example, the dispenser comprises a single section that is operable to dispense both the sanitizer substance and the hydrating substance. Accordingly, the dispenser facilitates that a user can dispense the substances with a reduced number of user actuations.

In particular, the sanitizer dispenser may be adapted for a so called "2-in-1" application of the sanitizer substance and hydrating substance.

The dispenser outlet may operable by touching, such as pushing. For example, the dispenser outlet may comprise one or more operating elements, which are touch-sensitive (e.g., can be moved, displaced, or depressed) and thereby can be operated by touching. Additionally or alternatively, the dispenser outlet may be operable by touch-free operation. For example, the dispenser outlet may comprise a sensor that is configured to detect one or more (spatial) conditions of an object (such as of a hand or finger), e.g., the presence and absence of the object (such as of a hand or finger), in the vicinity of the sensor, e.g. in front of the sensor. As such, based on the detected condition (such as the presence of the object) the dispenser outlet may operate to dispense the sanitizer substance and/or the hydrating substance. For example, a first detected condition operates the dispenser outlet to dispense the sanitizer substance, wherein a second detected condition operates the dispenser outlet to dispense the hydrating substance.

The compartments may be arranged adjacent to one another. Thereby, a compact container body is provided.

The container body may comprise a bottom and a top, wherein the compartments extend from the bottom to the top, and wherein the dispenser outlet is attached to the top. The bottom is typically the part of the container body upon which the sanitizer dispenser stands.

Preferably, at least part of the container body is transparent. Preferably, at least the second compartment and/or the first compartment is/are at least in part transparent. For example, at least part of the one or more walls or sidewalls comprised by the container body may be transparent.

The sanitizer substance may be a fluid and/or a liquid. The sanitizer substance may be an alcoholic composition, such as a hydroalcoholic composition. Preferably, the sanitizer substance is virucide. Additionally or alternatively, the sanitizer substance may be bactericidal, tuberculocidal, and/or fungicidal.

The sanitizer substance may comprises at least 20 wt. % alcohol, preferably at least 35 wt. % alcohol or at least 50 wt. % alcohol or at least 60 wt. % alcohol or at least 70 wt. % alcohol. The sanitizer substance may comprise at most 90 wt. % alcohol, preferably at most 80 wt. % alcohol or at most 70 wt. % alcohol or at most 65 wt. % alcohol. The sanitizer substance may comprises at least 20 wt. % water, preferably at least 30 wt. % water or at least 35 wt. % water or at least 50 wt. % water or at least 65 wt. % water or at least 80 wt. % water. The sanitizer substance may comprises at most 80 wt. % water, preferably at most 65 wt. % water or at most 50 wt. % water or at most 40 wt. % water. The water is preferably de-ionized water. The sanitizer substance may be in the form of a solution or a gel.

The hydrating substance may be a fluid or a liquid. The hydrating substance may be provided at least partly in the form of, or comprise, a cream and/or a body lotion. The hydrating substance may be a cream and/or a body lotion. The hydrating substance may be provided at least partly in the form of beads, such as hydrogel beads. Since the compartments effect that the sanitizing substance is separated from the hydrating substance, it is effectively prevented that the sanitizing substance, in particular alcohol provided therein, contracts the beads. Thereby, the beads are prevented from becoming hard and uncrushable and therefore, the dispenser effects that the sanitizing substance and the hydrating substance can be well used in combination.

Preferably, each bead is macroscopic and/or has a size comprised between 1 mm and 10 mm, more preferably between 1 mm and 7 mm.

Each bead may have an internal phase dispersed in a continuous phase, wherein the internal phase comprises a hydrophobic active ingredient, preferably a perfume oil and/or a flavor oil, wherein the continuous phase comprises a biopolymer and water and forms a hydrogel matrix, and wherein each bead comprises at least one liquid crystalline structured phase. In an embodiment, the hydrating substance may be the hydrogel bead disclosed in WO2019/077052 or EP3697503A.

The hydrating substance may be fragranced, preferably by a perfume oil and/or a flavor oil. Hence, the hydrating substance effects a very pleasant odor after sanitization by the sanitizer substance.

The sanitizer dispenser may be a consumer product, such as a perfuming consumer product. A "consumer product" (or "end-product") is to be understood as a manufactured product ready to be distributed, sold and used by a consumer. A "perfuming consumer product" is to be understood as a consumer product that is expected to deliver at least a pleasant perfuming effect to the surface to which it is applied (e.g. skin, hair, textile, or home surface). In particular, the sanitizer dispenser may be a package and/or a packaging solution.

According to a further aspect of the invention, a method for sanitizing is provided. The method comprises the steps of: a) providing a sanitizer dispenser as described above; b) dispensing the sanitizer substance from the first compartment; and c) dispensing the hydrating substance from the second compartment.

Preferably, step b) happens at least in part before and/or simultaneously to step c).

The above description and advantages regarding the apparatus apply analogously to the method.

DESCRIPTION OF PREFERRED EMBODIMENTS

Figure 2:
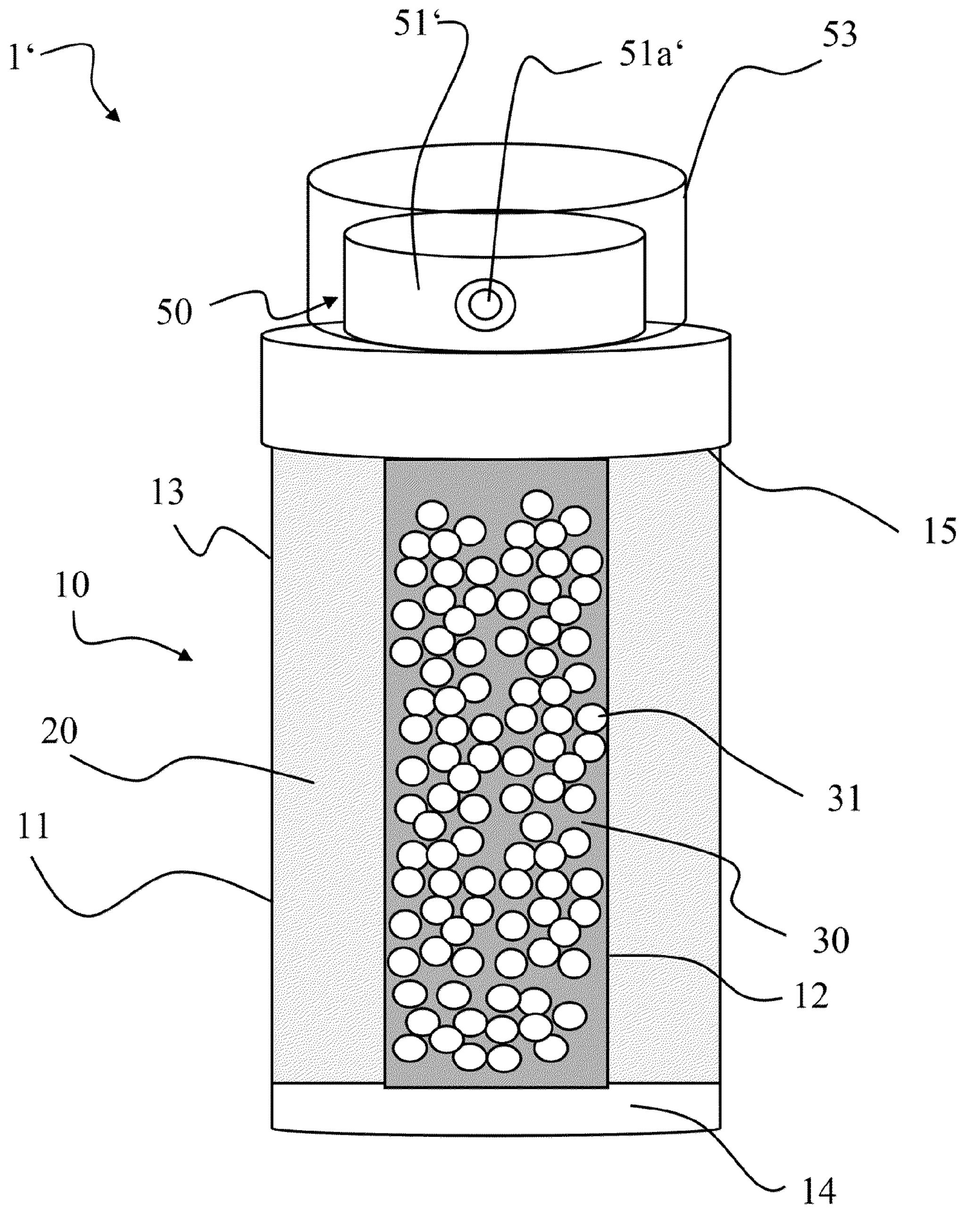
Figure 3:
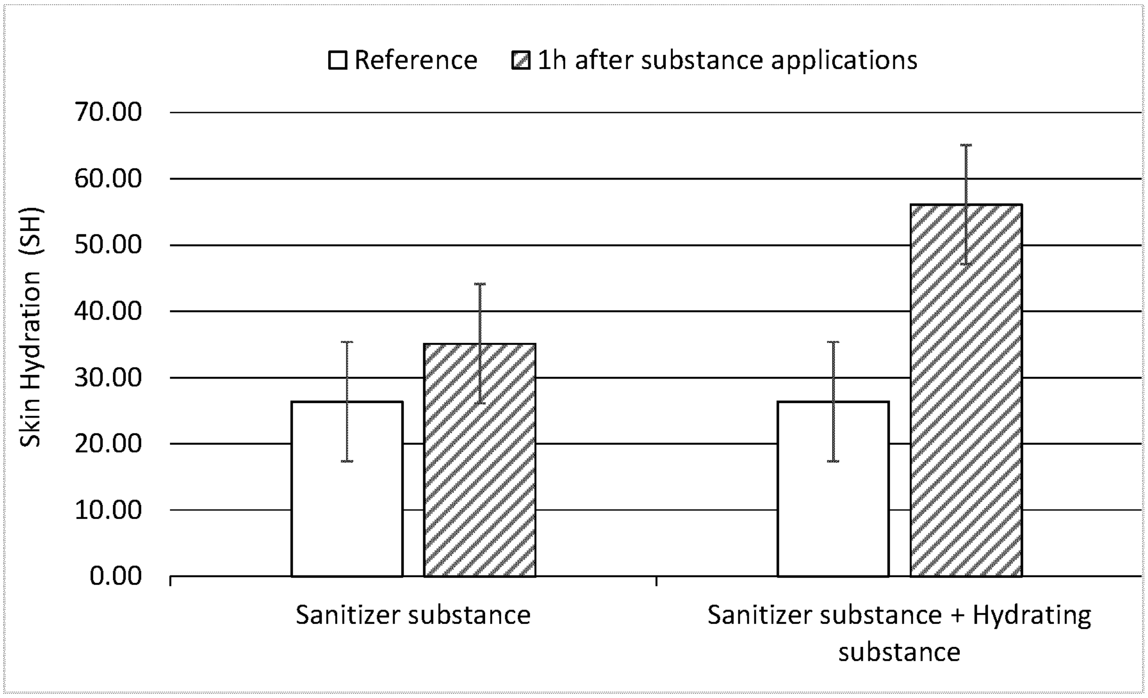
Figure 4:
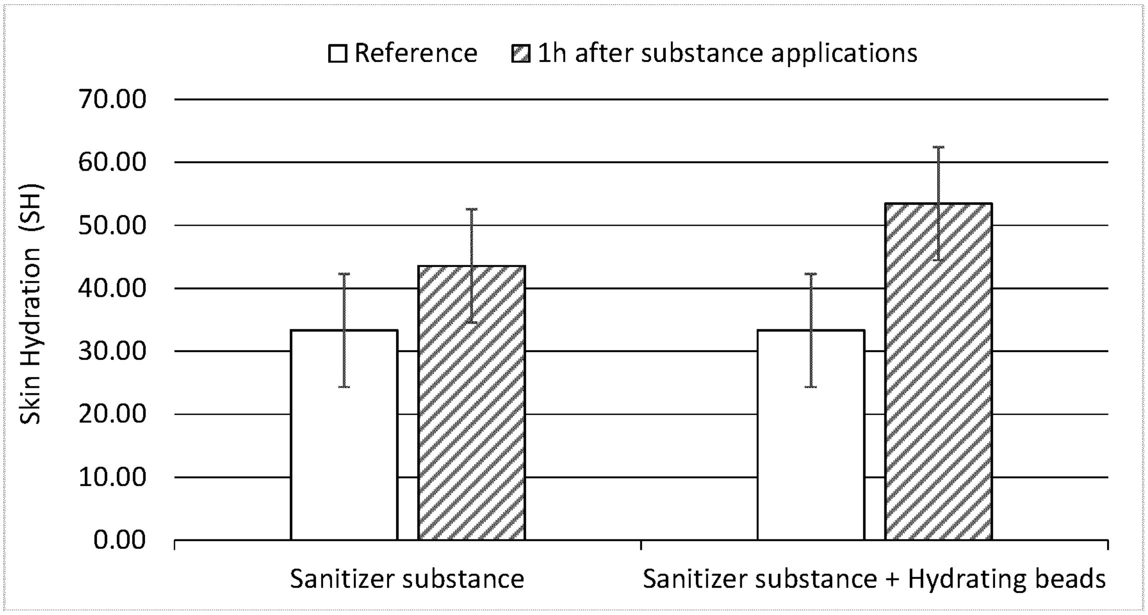

In the following, the invention is described exemplarily with reference to the enclosed figures, in which FIG. 1 shows a schematic perspective view of a sanitizer dispenser according to a first preferred embodiment of the invention;

FIG. 2 shows a schematic perspective view of a sanitizer dispenser according to a second preferred embodiment of the invention;

FIG. 3 is a diagram that shows the resulting Skin Hydration (SH) after application of only the sanitizer substance (left half of the diagram) compared to the resulting Skin Hydration after application of the sanitizer substance and the hydrating substance according to a first example of the invention (right half of the diagram); and FIG. 4 is a diagram that shows the resulting Skin Hydration after application of only the sanitizer substance (left half of the diagram) compared to the resulting Skin Hydration after application of the sanitizer substance and the hydrating substance according to a second example of the invention (right half of the diagram).

In FIG. 1, a preferred embodiment of a sanitizer dispenser 1 is exemplarily shown. The dispenser 1 is suitable for sanitizing surfaces such as the skin of a human. Preferably, the dispenser 1 is at least suitable for sanitizing the hands of a human. The dispenser 1 may have a handy size, such as for being placed on a tabletop and/or in a pocket. The dispenser 1 is not limited to a specific form. For example, the dispenser 1 has the form of a container, such as a bottle, and/or may be cylindrical in shape.

The dispenser 1 comprises a container body 10 with a first compartment 11 and a second compartment 12, which are separated from one another. In other words, the compartments 11, 12 can store respective components independent from one another. The container body 10 may have only one first compartment 11 and/or only one second compartment 12. As such, the dispenser 1 may be a dual-compartment dispenser, i.e. the container body 10 may be a dual-compartment container body or bottle. In other embodiments, the container body 10 may also have a plurality of first compartments 11 and/or a plurality of second compartments 12. The description regarding the first compartment 11 and the second compartment 12 then applies analogously to the one or more further first compartments 11 and the one or more further second compartments 12. One or more walls may be arranged to divide the container body 10 at least into the compartments 11, 12. The one or more walls may represent one or more sidewalls of the compartments 11, 12. The container body 10 may comprise a sidewall 13 that surrounds the compartments 11, 12. The sidewall 13 may be circular in cross-section. Other forms are also possible for the sidewall 13, such as an elliptical or polygonal form in the cross-section.

The compartments 11, 12 are not limited to a specific arrangement. As shown in FIG. 1, the compartments 11, 12 may be arranged adjacent to one another, e.g. with a (air) gap between them. In other embodiments, a sidewall of the first compartment 11 may at the same time form a sidewall of the second compartment 12, e.g. such that there is no (air) gap between the compartments 11, 12. In other words, a wall may divide the container body 10 into the first compartment 11 and the second compartment 12. In other embodiments, a plurality of first compartments may be arranged around one or more second compartments, and/or a plurality of second compartments may be arranged around one or more first compartments.

As shown in FIG. 1, the container body 10 preferably comprises a bottom 14 and a top 15, wherein the compartments 11, 12 may extend from the bottom 14 to the top 15. Each of the compartments 11, 12 may have a respective mouth that is arranged at the top 15. If the optional sidewall 13 is present, the sidewall 13 may extend from the bottom 14 to the top 15.

The container body 10 is not limited to a specific material. Preferably, at least part of the container body 10 is transparent. For example, the walls or sidewalls, which delimit the compartments 11, 12, may be transparent. Additionally or alternatively, the sidewall 13 may be transparent. The container body 10 may at least partly made of a resin, such as plastic, and/or glass. Additionally or alternatively, parts of the container body 10, such as the bottom 14, may be made from metal. Preferably, the bottom 14 may comprise a material that has a higher density than the material of the remainder of the container body 10. Thereby, a particular stable positioning of the dispenser 1 by way of the bottom 14 can be effected.

Each of the compartments 11, 12 is suitable for containing, i.e. storing, a respective substance, which may be provided in a fluidic and/or liquid form. For example, the compartments 11, 12 are designed in a leak-proof manner so that the contained substances cannot easily escape from the respective compartments. The amount storable by the first compartment 11 may be equal to the amount storable by the second compartment 12. Therefore, the compartments 11, 12 may have a substantially identical volume and/or substantially identical dimensions, such as an identical height and/or an identical width.

The first compartment 11 contains a sanitizer (i.e., disinfectant) substance 20. The substance 20 may be a formulation. The sanitizer substance 20 is a chemical agent designed to deactivate or destroy microorganisms on a surface, such as the skin. Preferably, the sanitizer substance 20 is virucide, which means that the substance 20 can deactivate or destroy viruses, such as coronaviruses (in particular SARS-COV-2 or other severe acute respiratory syndrome coronaviruses ("SARS-COV"), such as SARS-COV-1). Additionally or alternatively, the sanitizer substance 20 may be bactericidal, tuberculocidal, and/or fungicidal.

Preferably, the sanitizer substance 20 is an alcoholic composition, such as a hydroalcoholic composition. The sanitizer substance 20 may be provided as a solution and/or in the form of a liquid and/or gel. The sanitizer substance 20 may comprise alcohol, such as ethanol, preferably in the range from 20 wt. % to 80 wt. %, more preferably in the range from 50 wt. % to 70 wt. %, most preferably in the range from 55 wt. % to 65 wt. %. Additionally or alternatively, the sanitizer substance may comprise water, such as de-ionized water. The sanitizer substance 20 may comprise the water in the range from 20 wt. % to 80 wt. %, preferably from 30 wt. % to 50 wt. %, more preferably from 35 wt. % to 45 wt. %.

The second compartment 12 contains a hydrating substance 30. The substance 30 may be a formulation. The hydrating substance 30 is adapted to hydrate the skin of a human, e.g. of a human hand. In other words, the hydrating substance 30 is able to infuse cells, such as of the skin, with water or to retain the water produced by the body in the skin. Accordingly, the hydrating substance 30 can bring the skin from a dehydrated state into a hydrated state. The hydrating substance 30 may comprise a cream and/or a body lotion. Preferably, the hydrating substance 30 is provided at least partly in the form of beads 31, such as hydrogel beads. Each bead 31 may be macroscopic and/or may have a size comprised between 1 mm and 10 mm. The beads 31 may be spherical. Each bead 31 may have an internal phase dispersed in a continuous phase, wherein the internal phase comprises a hydrophobic active ingredient, preferably a perfume oil and/or a flavor oil, wherein the continuous phase comprises a biopolymer and water and forms a hydrogel matrix, and wherein each bead 31 comprises at least one liquid crystalline structured phase. The beads 31 may be so called "crystalline fragranced pearls". Preferably, at least part of the beads 31 may be like the hydrogel bead disclosed in WO2019/077052, the contents of which is also included by reference.

The hydrating substance 30 may be fragranced. As such, the hydrating substance 30 may effect a pleasant odor. To be fragranced, the hydrating substance 30 may comprise a fragrance and/or flavoring substance, such as a perfume and/or a perfume oil and/or a flavor oil. The "perfume oil" is an ingredient or composition that is a liquid at about 20° C. The perfume oil may be a perfuming ingredient alone or a mixture of ingredients in the form of a perfuming composition. A "perfuming ingredient" is a compound, which is used for the primary purpose of conferring or modulating an odor. In other words, such an ingredient, to be considered as being a perfuming one, must be recognized by a person skilled in the art as being able to at least impart or modify in a positive or pleasant way the odor of a composition, and not just as having an odor. The perfume oil may include a combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn (rosin resins, available from Eastman), benzyl benzoate, ethyl citrate, limonene or other terpenes, or isoparaffins. Preferably, the solvent is very hydrophobic and highly sterically hindered, like for example Abalyn or benzyl benzoate. Preferably, the perfume comprises less than 30% of solvent. More preferably, the perfume comprises less than 20% and even more preferably less than 10% of solvent, all these percentages being defined by weight relative to the total weight of the perfume. Most preferably, the perfume is essentially free of solvent.

The sanitizer dispenser 1 further comprises a dispenser outlet 50 that is attached to the container body 10 and configured to dispense the sanitizer substance 20 from the first compartment 11 and the hydrating substance 30 from the second compartment 12. The dispenser outlet 50 is thus fluidly connected to the first compartment 11, e.g. via a first fluid line (such as a pipe), and to the second compartment 12, e.g. via a second fluid line (such as a pipe). The dispenser outlet 50 may comprise one or more pumps arranged to move and thus dispense the substances 20, 30 from their compartments 11, 12, respectively. The one or more pumps may be operated by manual operation (such as by a hand or a finger of a human) and/or by electrical energy. For the latter, the sanitizer dispenser 1, such as the dispenser outlet 50, may comprise an electric motor and/or an electrical energy storage such as a battery for delivering the electrical energy to the one or more pumps. Additionally or alternatively, the dispenser outlet 50 may be configured to dispense the substances 20, 30 from their respective compartments 11, 12 by gravity and/or by manipulating (such as squeezing) the container body 10.

In the embodiment shown in FIG. 1, the dispenser outlet 50 is configured to dispense selectively the sanitizer substance 20 or the hydrating substance 30 or both of them together. Therefore, the dispenser outlet 50 can dispense the substances 20, 30 independent from one another. As such, a user of the dispenser 1 has the choice to dispense the sanitizer substance 20 or the hydrating substance 30; thus, the dispenser 1 may be a so-called "dual independent" application. For example, the user may first dispense the sanitizer substance 30 to disinfect her or his skin (such as of the hand) and subsequently dispense the hydrating substance 30 for preventing the skin from dehydrating. As shown in FIG. 1, the dispenser outlet 50 may comprise a first section 51 and a second section 52, which are independently operable from one another. The first section 51 is operable to dispense the sanitizer substance 20. For example, the first section 51 comprises a respective (or own) pump that is configured to move (e.g., draw) the sanitizer substance 20 from the first compartment 11. In particular, the first section 51 may be manually operated (such as by touching, e.g. pushing) to thereby operate the respective pump and thus dispense the sanitizer substance 20. As such, the first section 51 may be moved from an initial position into an operated position (such as a depressed position) in order to operate the respective pump. The first section 51 may comprise a respective dispensing opening 51*a*, by way of which the sanitizer substance 20 is dispensed (i.e., discharged) from the dispenser outlet 50.

The second section 52 is operable to dispense the hydrating substance 30. Dispensing by the second section 52 may be identical to dispensing by the first section 51. For example, the second section 52 comprises a respective (or own) pump that is configured to move (e.g., draw) the hydrating substance from the second compartment 12. In particular, the second section 52 may be manually operated (such as by touching, e.g. pushing) to thereby operate the respective pump and thus dispense the hydrating substance 30. As such, the second section 52 may be moved from an initial position into an operated position (such as a depressed position) in order to operate the respective pump. The second section 52 may comprise a respective dispensing opening 52*a*, by way of which the hydrating substance 30 is dispensed (i.e., discharged) from the dispenser outlet 50.

As shown in FIG. 1, the first section 51 may be arranged adjacent to the second section 52. The invention is however not limited to a specific arrangement of the sections 51, 52. In other embodiments, the container body 10 may be arranged between the sections 51 and 52, e.g. such that the first section 51 is arranged above the top 15 of the container body 10 and the second section is arranged below the bottom 14 of the container body 10. Further, one of the sections 51, 52 may be arranged at least partly in the respective other section, e.g. in such a way that the sections 51, 52 are stacked into each other. When the sections 51, 52 are arranged adjacent to one another, the sections 51, 52 may be at least in part flush with one another and/or the dispensing openings 51*a*, 52*a* may be positioned on substantially the same height. The height is measured from the bottom 14 of the container body 10.

In the embodiment shown in FIG. 1, the dispenser outlet 50 is operable by touching, namely by pushing. Additionally or alternatively, other possibilities for operating the dispenser outlet 50 by touching are possible, such as by displacement or pulling. In other embodiments, the dispenser outlet 50 may be operable by touch-free operation. This may be realized by providing one or more sensors arranged to detect the state (e.g. presence and absence) of an object (e.g. hand or finger) and to dispense the respective substance based on the detected state, e.g. when the presence of an object is detected. For example, each of the sections 51, 52 may comprise a respective sensor in order to operate the respective section by touch-free operation and thus dispense the respective substance.

As shown in FIG. 1, the dispenser outlet 50 is preferably attached to the top 15 of the container body 10. In other embodiments, the dispenser outlet 50 may be attached to a different position, such as on a lateral side of the container body 10 (e.g., to the sidewall 13) or to the bottom 14 of the container body 10. Attachment of the dispenser outlet 50 may be done with a mechanical connection such as a force and/or form fit. For example, the dispenser outlet 50 may be attached to the container body 10 by engaging a part of the container body 10, such as the one or more walls, which delimit the compartments 11, 12, and/or the sidewall 13. The engagement may be a snap engagement and/or a press-fit and/or a threading engagement.

According to an embodiment, the dispenser outlet may be configured such that, upon operation of the dispenser outlet, both the sanitizer substance 20 dispenses from the first compartment 11 and the hydrating substance 30 dispenses from the second compartment 12. With respect to the dispenser outlet 50, this may be achieved by integrally forming the first section 51 with the second section 52. Thereby, the sections 51, 52 represent a section that, when operated, simultaneously dispenses the substances 20, 30. When discharged from the dispenser outlet 50, the substances 20, 30 may mix with one another. For example, the dispensing openings 51*a*, 52*a* may be arranged in such a way (e.g. inclined to one another) that the substances 20, 30 mix (or merge) with one another shortly after they are discharged from the respective openings 51*a*, 52*a*. That is, the substances may combine, or merge, on the surface, such as the skin.

The sanitizer dispenser 1 may further comprise a cap 53 arranged to cover at least part of the dispenser outlet 50, such as at least the dispensing openings 51*a*, 52*a*. The cap 53 may be transparent and/or may be attached to the dispenser 1, such as to the dispenser outlet 50. This attachment may be achieved by a force and/or form fit, such as by a press fit. The cap 53 may be cylindrical in shape but may also have different shapes. When attached, the cap 53 may cover the dispenser outlet 50 to prevent the dispenser outlet 50 from being (accidentally) operated.

FIG. 2 shows a second preferred embodiment of a sanitizer dispenser 1'. The sanitizer dispenser 1' corresponds to the sanitizer dispenser 1 described above, unless otherwise described in the following. Same reference numerals indicate same features.

The dispenser 1' differs from the dispenser 1 according to the first embodiment in particular in that its dispenser outlet 50' is alternatively designed. The dispenser outlet 50' comprises a section 51' that is operable to dispense both the sanitizer substance 20 and the hydrating substance 30. As such, the dispenser 1' may be a so called “2-in-1” application. For example, the dispenser outlet 50' has such a configuration that, upon its operation (such as of the section 51'), the sanitizer substance 20 and the hydrating substance 30 are dispensed (i.e., discharged) from the dispenser outlet 50' in a defined manner or sequence. This configuration may be such that a defined amount of the sanitizer substance 20 dispenses at least in part (or completely) before a defined amount of the hydrating substance 30 dispenses. For example, the section 51' comprises one or more pumps configured to move (e.g., draw) the sanitizer substance 20 from the first compartment 11 and the hydrating substance 30 from the second compartment 12 in a defined sequence, e.g. such that dispensing the sanitizer substance 20 happens at least in part before and/or at least in part simultaneously to dispensing the hydrating substance 30. The one or more pumps may in particular correspond to the one or more pumps described above with respect to the dispenser 1.

For example, the one or more pumps may be configured to draw and thus dispense only the sanitizer substance 20 in a first phase (e.g., as the section 51' is moved, such as depressed, into a first position) and to draw and thus dispense the hydrating substance 30 in a second phase that follows the first phase (e.g., as the section 51' is moved, such as depressed, from the first position into a second position). The sanitizer substance 20 may be dispensed only in the first phase or may be also dispensed in the second phase so that there is a partial simultaneous dispensing of the substances 20, 30. Alternatively, the one or more pumps may be configured to start drawing and thus dispensing of the substances 20, 30 at the same time, when the dispenser outlet 50' is operated. Therefore, when operated, the dispenser outlet 50' will always simultaneously dispense the sanitizer substance 20 and the hydrating substance 30.

The dispenser outlet 50' may comprise a mixing chamber that fluidly connects to the compartments 11 and 12. The mixing chamber is arranged such that, as the dispenser outlet 50' draws, e.g. with its one or more pumps, the substances 20, 30 from the compartments 11, 12, the substances 20, 30 will merge or mix in the mixing chamber to be subsequently dispensed from the mixing chamber and thus from the dispenser outlet 50'. As such, the substances are simultaneously dispensed by the dispenser outlet 50'. The substances 20, 30 may then be dispensed via a single dispensing opening 51*a*' comprised by the dispenser outlet 50' (e.g., by the first section 51') and fluidly connected to the mixing chamber.

Alternatively, the dispenser outlet 50' may be designed in such a way that the substances 20, 30 mix with one another as they are discharged from the dispenser outlet 50; as such, the mixing chamber is not necessary. The dispenser outlet 50' may then comprise the single dispensing opening 51*a*' in such a way that the substances 20, 30 mix with one another in the single dispensing opening 51*a*'. For example, the first line for drawing the sanitizer substance 20 and the second line for drawing the hydrating substance 30 may open (with their downstream openings) into the single dispensing opening 51*a*'. Thereby, the substances 20, 30 can mix or combine in the dispensing opening 51*a*' to be subsequently applied to a surface, such as a skin.

As an alternative to the single dispensing opening 51*a*', the dispenser outlet 50' may comprise a respective dispensing opening for each of the substances 20, 30. For example, the dispenser outlet 50' may have the dispensing opening 51*a*' as a first dispensing opening for dispensing (or discharging) the sanitizer substance 20, wherein the dispenser outlet 50' comprises a second dispensing opening for dispensing the hydrating substance 30. The second dispensing opening may be arranged congruent with the first dispensing opening 51*a*'. As such, the substances 20, 30 can be dispensed via the dispensing opening and thus mix (or merge) with one another shortly after they are discharged from the respective openings.

The section 51' may substantially correspond to the first section 51 and, thus, may be manually operated (such as by touching, e.g. pushing) to thereby operate the one or more pumps and thus dispense the substances 20, 30. For example, the section 51' may be moved from an initial position into an operated position (such as a depressed position) in order to operate the one or more pumps.

EXAMPLES

Example 1: Hydroalcoholic Gel in Combination with a Hydrating Substance in the Form of a Cream The sanitizer substance 20 was prepared by mixing the ingredients in table 1 below, thereby obtaining a hydroalcoholic gel.

TABLE 1

Composition of the sanitizer substance

| Ingredients | Effective Amount of Ingredient (% wt) | Function |
|---|---|---|
| Ethanol | 70 | Solvent |
| De-ionized (DI) water | 22 | Solvent |
| Acrylates Copolymer | 6 | Thickening polymer |
| Glycerol | 1 | Humectant |
| NaOH (18%) | 1 | Neutralizing agent |

The sanitizer substance 20 was then provided in the first compartment 11.

In a further step, the hydrating substance 30 was prepared by mixing the ingredients in table 2 below, thereby obtaining a hydrating fragranced substance in the form of a cream.

TABLE 2

Composition of the hydrating substance

| INCI_NAME | Concentration % wt | Function |
|---|---|---|
| Steareth-2 (and) PEG-8 Distearate | 5 | Emulsifier |
| Cetyl alcohol | 0.5 | Emulsion Stabiliser |
| Ceteth-20 (and) Glyceryl Stearate (and) PEG-6 Stearate (and) Steareth-20 | 4 | Emulsifier |
| Squalan | 1 | Emollient |
| Paraffin Oil | 2 | Emollient |
| Petrolatum | 5.5 | Emollient |
| Water deionised | 75.9 | Solvent |
| Propylene glycol | 5 | Humectant |
| Sodium Carbomer | 0.2 | Emulsion Stabiliser |
| Fragrance | 0.3 | Fragrance |
| Phenoxyethanol (and) piroctone olamine | 0.6 | Preservative |

The hydrating substance 30 was then provided in the second compartment 12.

Before the substances 20, 30 have been applied to the skin (of an arm), the Skin Hydration (SH) was measured in-vivo using a Moisturemeter SC device of the company Delfin Instruments. Thereby, a reference hydration skin value (SH0) of the skin has been obtained. The measurements were done on two different spots of the forearm. Thereby, reference hydration skin values (SH0) of the skin have been obtained.

Then, 50 μl of the sanitizer substance 20 have been applied on each spot of the skin and spread by five finger rounds. Then, 5 minutes after sanitizer substance application, 50 μl of the hydrating substance 30 have been applied on one of the two spot. 1 h after application, the remaining substances were removed with a tissue and the SH was measured on each spot. The results are shown in the right half of the diagram in FIG. 3.

Example 2: Hydroalcoholic Gel in Combination with a Hydrating Substance in the Form of Beads The sanitizer substance 20 was prepared by mixing the ingredients in table 3 below, thereby obtaining a hydroalcoholic gel.

TABLE 3

Composition of the sanitizer substance

| Ingredients | Effective Amount of Ingredient (% wt) | Function |
|---|---|---|
| Ethanol | 70 | Solvent |
| De-ionized (DI) water | 22 | Solvent |
| Acrylates Copolymer | 6 | Thickening polymer |
| Glycerol | 1 | Humectant |
| NaOH (18%) | 1 | Neutralizing agent |

The sanitizer substance 20 was then provided in the first compartment 11.

In a further step, the hydrating substance 30 was prepared by dispersing hydrating alginate fragranced beads in a hydrogel. Such beads were prepared using the ingredients in table 4 below.

TABLE 4

Composition of the hydrating pearls

| Ingredients | Effective Amount of Ingredient (% wt) | Function |
|---|---|---|
| Sodium alginate | 0.68 | Gelling agent |
| De-ionized water | 33.32 | Solvent |
| Glycerol stearate citrate | 6 | Surfactant |
| Fragrance | 5 | Fragrance |
| Internal Body Cream | 55 | Hydrating body cream |

Sodium alginate, water and glycerol stearate citrate were mixed and stirred for 1 h at 70° C. The solution was cooled down under stirring to reach room temperature. Fragrance and internal body cream were added to the solution and the mixture was stirred for 15 min. Then, the alginate fragranced beads were formed by prilling the mixture in a 0.5% CaCl2 aqueous solution. The beads were filtered, washed with deionized water and added in the hydrogel (ratio 3:2, pearls: hydrogel) to form the hydrating substance. The hydrogel was prepared by mixing the ingredients in table 5 below.

TABLE 5

Composition of the hydrogel

| Ingredients | Effective Amount of Ingredient (% wt) | Function |
|---|---|---|
| Water | 98.4 | Solvent |
| Polyacrylate Crosspolymer-6 | 1 | Thickening polymer |
| Phenoxyethanol | 0.6 | Preservative |

The hydrating substance 30 was then provided in the second compartment 12.

Before the substances 20, 30 have been applied to the skin (of an arm), the Skin Hydration (SH) was measured in-vivo using a Moisturemeter SC device of the company Delfin Instruments. The measurements were done on two different spots of the forearm. Thereby, reference hydration skin values (SH0) of the skin have been obtained.

Then, 50 μl of the sanitizer substance 20, have been applied on each spot of the skin and spread by five finger rounds. Then, 5 minutes after sanitizer substance application, 50 μl of hydrating substance (30+31) have been applied on one of the two spot. 1 h after application, the remaining substances were removed with a tissue and the SH was measured on each spot. The results are shown in the right half of the diagram in FIG. 4.

In each diagram of FIGS. 3 and 4, a comparative example is shown in the left half. In these comparative examples, only the sanitizer substance 20 has been applied (namely 50 μl), i.e. the respective hydrating substances 30, 31 have not been applied. In the right half of each diagram in FIGS. 3 and 4, the respective example of the present invention is shown, namely examples 1 and 2, respectively. One can see that after 1 h after the sanitizer substance 20 has been applied, the examples 1 and 2 according to the invention effect a higher skin hydration than in the comparative example and thus effectively prevent a dehydration of the skin. At the same time, the sanitizer substance 20 effects a sanitization of the skin. Further, the fragrance in the hydrating substance can prevent the formation of an unpleasant odor due to the sanitizer substance.

It should be clear to a skilled person that the embodiments shown in the figures are only preferred embodiments, but that, however, also other designs of a sanitizer dispenser can be used.

The invention claimed is:

1. A sanitizer dispenser (1, 1'), comprising:

a container body (10) with a first compartment (11) and a second compartment (12), which are separated from one another, wherein the first compartment (11) contains a sanitizer substance (20), and wherein the second compartment (12) contains a hydrating substance (30); and a dispenser outlet (50, 50') attached to the container body (10) and configured to dispense the sanitizer substance (20) from the first compartment (11) and the hydrating substance (30) from the second compartment (12);

wherein the sanitizer substance (20) is an alcoholic composition comprising at least 20 wt. % alcohol and at most 90 wt. % alcohol; and wherein the hydrating substance (30) is provided at least partly in the form of beads (31).

2. The sanitizer dispenser (1, 1') according to claim 1, wherein the dispenser outlet (50, 50') is configured such that, upon operation of the dispenser outlet (50, 50'), both the sanitizer substance (20) dispenses from the first compartment (11) and the hydrating substance (30) dispenses from the second compartment (12).

3. The sanitizer dispenser (1) according to claim 1, wherein the dispenser outlet (50) comprises a first section (51) and a second section (52), which are independently operable from one another, wherein the first section (51) is operable to dispense the sanitizer substance (20), and wherein the second section (52) is operable to dispense the hydrating substance (30).

4. The sanitizer dispenser (1') according to claim 1, wherein the dispenser outlet (50') comprises a section (51') operable to dispense both the sanitizer substance (20) and the hydrating substance (30).

5. The sanitizer dispenser (1, 1') according to claim 1, wherein the dispenser outlet (50, 50') is operable by touching and/or by touch-free operation.

6. The sanitizer dispenser (1, 1') according to claim 1, wherein the compartments (11, 12) are arranged adjacent to one another, and/or wherein the container body (10) includes one or more walls, which divide the container body (10) into the compartments (11, 12).

7. The sanitizer dispenser (1, 1') according to claim 1, wherein the container body (10) comprises a bottom (14) and a top (15), wherein the compartments (11, 12) extend from the bottom (14) to the top (15), and wherein the dispenser outlet (50, 50') is attached to the top (15).

8. The sanitizer dispenser (1, 1') according to claim 1, wherein at least part of the container body (10) is transparent.

9. The sanitizer dispenser (1, 1') according to claim 1, wherein the sanitizer substance (20) is in the form of a solution or a gel.

10. The sanitizer dispenser (1, 1') according to claim 1, wherein each bead (31) has an internal phase dispersed in a continuous phase, wherein the internal phase comprises a hydrophobic active ingredient, wherein the continuous phase comprises a biopolymer and water and forms a hydrogel matrix, and wherein each bead comprises at least one liquid crystalline structured phase.

11. The sanitizer dispenser (1, 1') according to claim 1, wherein the hydrating substance (30) is provided at least partly in the form of a cream and/or a body lotion.

12. The sanitizer (1, 1') dispenser according to claim 1, wherein the hydrating substance (30) is fragranced.

13. A method for sanitizing, comprising the steps of:

a) providing a sanitizer dispenser (1, 1') according to claim 1, b) dispensing the sanitizer substance (20) from the first compartment (11), and c) dispensing the hydrating substance (30) from the second compartment (12).

14. The method according to claim 13, wherein step b) happens at least in part before and/or simultaneously to step c).

15. The sanitizer dispenser (1, 1') according to claim 2, wherein dispensing the sanitizer substance (20) happens at least in part before and/or simultaneously to dispensing the hydrating substance (30).

16. The sanitizer dispenser (1) according to claim 3, wherein the first section (51) is arranged adjacent to the second section (52).

17. The sanitizer dispenser (1') according to claim 4, wherein the dispenser outlet (50') comprises a section (51') operable to dispense both the sanitizer substance (20) and the hydrating substance (30) via a single dispensing opening (**51*a'***).

18. The sanitizer dispenser (1, 1') according to claim 8, wherein the second compartment (12) is transparent.

* * * * *